US006554802B1

(12) United States Patent
Pearson et al.

(10) Patent No.: US 6,554,802 B1
(45) Date of Patent: Apr. 29, 2003

(54) MEDICAL CATHETER ANCHOR

(75) Inventors: Robert M. Pearson, Woodbury, MN (US); Douglas O. Hankner, St. Paul, MN (US); Weiping Yu, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/281,863

(22) Filed: Mar. 31, 1999

(51) Int. Cl.$^7$ ................................................ A61M 5/32
(52) U.S. Cl. .................. 604/177; 604/165.03; 604/174
(58) Field of Search ................................ 604/174, 177, 604/164.01, 164.07, 165.01, 165.03, 171, 264, 160, 161, 528, 533, 535, 538

(56) References Cited

U.S. PATENT DOCUMENTS

| | | | |
|---|---|---|---|
| 3,589,361 A | * 6/1971 | Loper et al. ............ 604/165.03 |
| 3,598,118 A | * 8/1971 | Warren ........................ 604/508 |
| 4,366,817 A | 1/1983 | Thomas ....................... 604/174 |
| 4,645,492 A | 2/1987 | Weeks ......................... 604/174 |
| 4,802,947 A | * 2/1989 | Bartholomew ............ 156/380.5 |
| 5,267,971 A | * 12/1993 | Brimhall ..................... 604/177 |
| 5,464,446 A | 11/1995 | Dreessen et al. ........... 607/116 |
| 5,489,273 A | * 2/1996 | Whitney et al. ............ 604/160 |
| 5,578,013 A | 11/1996 | Bierman ..................... 604/180 |
| 5,584,874 A | 12/1996 | Rugland et al. ............ 607/132 |
| 5,702,371 A | 12/1997 | Bierman ..................... 604/180 |
| 5,843,146 A | 12/1998 | Cross, Jr. .................... 607/115 |
| 5,843,150 A | 12/1998 | Dreessen et al. ........... 607/116 |

* cited by examiner

*Primary Examiner*—Brian L. Casler
*Assistant Examiner*—Jennifer Maynard
(74) *Attorney, Agent, or Firm*—Banner & Witcoff, Ltd.

(57) ABSTRACT

The present invention provides an anchor for securely positioning a catheter intended to deliver drug or other medicaments to a desired position in tissue wherever found in the body or in epidural or intrathecal space of a spinal cord or brain. The present invention comprises, in the preferred embodiment, a generally tubular body for receiving the catheter and a pair of wings to assist in securing the device. The body has a slot that extends through the body between the wings. The wings and the slot cooperate so that the opposed edges of the slot just come together as the wings are brought into contact with each other. The wings interact with the slot to radially compress the catheter within the lumen of the tubular body to hold the catheter in a fixed relation to the tubular body. In addition, the wings allow the device to be sutured to tissue to secure and fix the device to tissue. A first suture is placed around the base of the wings very near where the wings contact the body of the anchor. A second suture secures the wings together and affixes the anchor to the patient's tissue.

13 Claims, 4 Drawing Sheets

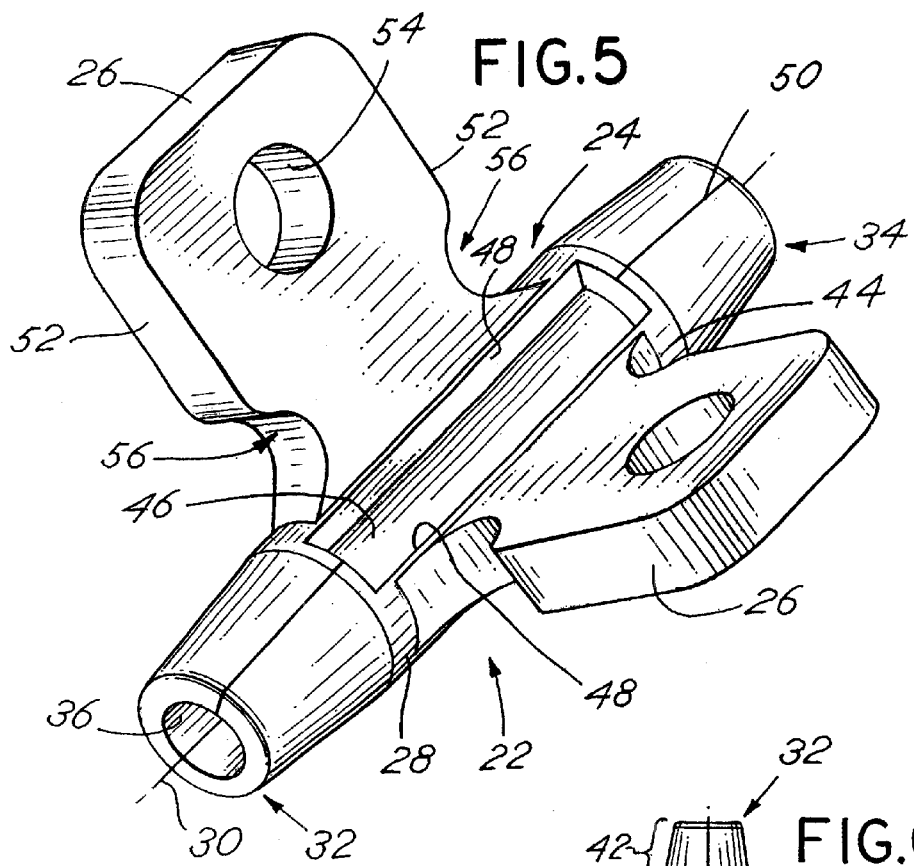
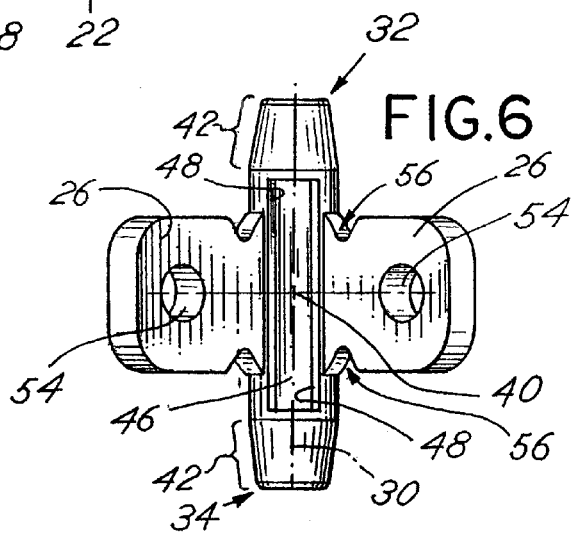
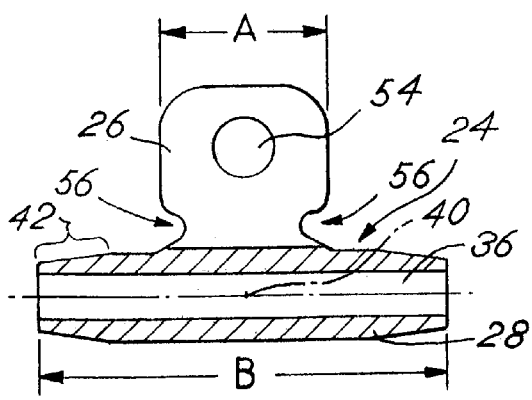
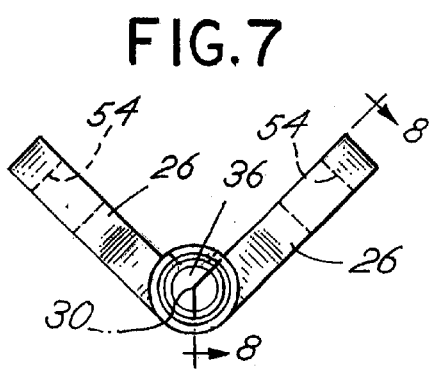

MEDICAL CATHETER ANCHOR

BACKGROUND OF THE INVENTION

1. Field of the Invention

This invention relates generally to the techniques for devices for delivering medicaments to selected sites in tissue. Specifically, this invention relates to an apparatus for securingly positioning a drug or medication delivering catheter after the catheter is positioned in the brain, spinal epidural space, the intrathecal space or in a peripheral nerve application or in other tissue.

2. Description of the Related Art

Medication delivery to the brain, spinal cord, cerebrospinal fluid or other tissue throughout the body is useful in treating many maladies, diseases and illnesses. Through the use of an implantable pump and catheter, precise drug doses can be directly delivered to the area of interest to treat the malady, disease or illness or its symptoms.

Controlled placement of drug delivering catheters in the position of interest is highly desirable. This allows highly concentrated drugs or other medicaments to be delivered to a specific site where, because the drug or medicament is highly concentrated, the therapeutic effect will be maximized. Further, because only a small amount of such highly concentrated drug or medicarnent is needed at the site to be therapeutically beneficial, side effects from receiving relatively large doses of the drug orally or intravenously are minimized.

In view of the desirability of placing the highly concentrated drug or medicament at a specific site, movement of the catheter from its desired position is highly problematic. This is a problem known as "dislodgment". Dislodgment means that the distal tip of the catheter is moved enough from its desired position for the therapy to be affected. For some therapies, for example, intrathecal administration of drugs to the spinal cord, movement on the order of 0.5 inch or less may cause a noticeable decrease in therapy. For others, such as when a catheter is implanted in the intrathecal space of the spinal cord, the catheter must exit the intrathecal space to cause a change in therapy. This can be as much as 8 inches.

It is rare for the anchor to move relative to the tissue it is attached to. It is much more likely for the catheter to move relative to the anchor (slip through). Where the catheter is implanted in the spine, an anchor is typically placed outside the spine and is anchored to a ligament. In this case, it is not uncommon for the catheter to exit the spine and "bunch up" just distal to the anchor between the anchor and the entrance to the spine.

Dislodgment causes the highly concentrated drug or other medicament to not be delivered to the desired location. As a result, the desired therapeutic effect is not achieved. In addition, applying the highly concentrated drug or medicament to another site may produce undesired effects. Therefore, dislodgment is a condition to be avoided.

There are currently several ways physicians attempt to solve the problem of dislodgment. One way is to suture the catheter to tissue to "anchor" the catheter to the tissue. A problem with this approach is that often the suture cuts through or occludes the catheter thereby disabling the catheter. This prevents the desired drug or medicament from passing to the distal end of the catheter to be delivered to the target site. In addition, the drug or medicament then leaks out of the cut area where it may possible cause undesirable effects.

Another way to solve the dislodgment problem is to place an "anchor" around the catheter and then secure the anchor to tissue. In this way, the anchor prevents the catheter from moving relative to the anchor and the anchor itself is prevented from moving relative to tissue because the anchor is securely fastened to the tissue.

An example of such an anchor is shown in FIGS. 1–4 labeled generally 2. The anchor 2 has a tubular body 4 and a pair of opposed wings 6. Body 4 has a central channel 8. Central channel 8 is typically sized to be the same diameter as the outer diameter of a catheter 14 that is to be secured by the anchor 2. Body 4 often has a longitudinal slit 10 that extends entirely through body 4 along the entire length of body 4.

The wings 6 each have an eyelet 12. In use, a catheter 14 is placed through slit 10 into channel 8. Because of the tight tolerance in the diameter of central channel 8 and the outer diameter of catheter 14, it is very difficult if not impossible to thread catheter 14 through channel 8. Thereafter, anchor 2 is moved to the desired position. Wings 6 are pinched together toward slit 10. A suture 16 is placed through eyelets 12 and tissue 18 to secure the catheter 14 in the anchor 2 and anchor 2 to tissue 18 (FIG. 4).

A problem with this design for anchor 2 is that as wings 6 are brought together, the material of body 4 develops hoop stresses. Hoop stresses are the stresses that develop as a tightening force is applied to a hoop and the hoop resists being inwardly compressed. In this case, the hoop is the cross-section of the body 4 of the anchor 2. The tightening force is the application of force to the body 4 by bringing wings 6 together. These hoop stresses take a substantial amount of the energy provided by moving the wings 6 together and store it in tension within the material of body 4. As a result, a seriously reduced amount of energy is available for contacting the outer surface of the catheter to cause frictional contact with the catheter to hold it in place with respect to the anchor 2.

Another problem occurs because anchor 2 is placed in a pocket 20 formed in tissue 18 in a patient's body. A problem with this anchor 2 is that it is difficult bring the wings 6 from their 180° opposed position to their pinched position in the small opening provided by in the pocket in the tissue 18. This problem is exacerbated when the surgeon also has to open slit 10 and place the catheter 14 in the central channel 8. This is often accomplished by bending wings 6 together on the opposite side of body 4 so that slit 10 opens. This requires a very dexterous maneuver in the small space presented by the pocket 20 in the tissue 18. Often, it takes several tries to get the catheter 14 positioned within central channel 8 through slit 10. This complicates the surgery with the concomitant chance or problems or complications.

SUMMARY OF THE INVENTION

The present invention provides an anchor for securely positioning a catheter intended to deliver drug or other medicaments to a desired position in tissue wherever found in the body or in epidural or intrathecal space of a spinal cord or brain. The present invention comprises, in the preferred embodiment, a generally tubular body for receiving the catheter and a pair of wings to assist in securing the device. The body has a slot that extends through the body between the wings. The wings and the slot cooperate so that the opposed edges of the slot just come together as the wings are brought into contact with each other. In this way, hoop forces are virtually eliminated so that all the stress produced by bringing the wings together is applied to the catheter to frictionally hold the catheter in position within the anchor. The wings interact with the slot to radially compress the catheter within the lumen of the tubular body to hold the catheter in a fixed relation to the tubular body.

In addition, the wings allow the device to be sutured to tissue to secure and fix the device to tissue. A first suture is placed around the base of the wings very near where the wings contact the body of the anchor. A second suture secures the wings together and affixes the anchor to the patient's tissue. This suture is placed through an eyelet in each of the wings. In this way, the normal stresses applied to the catheter by bringing the wings together are maximized.

In use the catheter is placed in the central channel of the anchor. The wings are brought together and sutured. The wings are then sutured to the patient's tissue.

It is an object of the present invention to provide an anchor that securely holds a catheter without crushing, kinking, pinching or occluding the catheter.

It is another object of the invention to provide an anchor can be securely attached to a patient's tissue.

It is another object of the invention to provide an anchor that is easy to use.

The proposed design addresses these objects. Movement of the catheter relative to the anchor is greatly decreased because of the holding force provided as the wings are brought together and secured. Because the anchor is smaller and easier to place than known anchors, the physician should be able to place the anchor closer to the spinal entry site. This should make it unlikely that the catheter will pull out of the implant site and bunch up as the patient moves.

BRIEF DESCRIPTION OF TIE DRAWING

The preferred embodiment of the invention is illustrated in the drawing, wherein like reference numerals refer to like elements in the various views, and wherein:

FIG. 5 is a perspective view of the preferred anchor of the present invention.

FIG. 6 is a top view of the anchor of FIG. 5.

FIG. 7 is an end view of the anchor of FIG. 5.

FIG. 8 is a side cross-sectional view of the anchor of FIG. 5.

DETAILED DESCRIPTION OF THE PREFERRED EMBODIMENT

Figure 1:
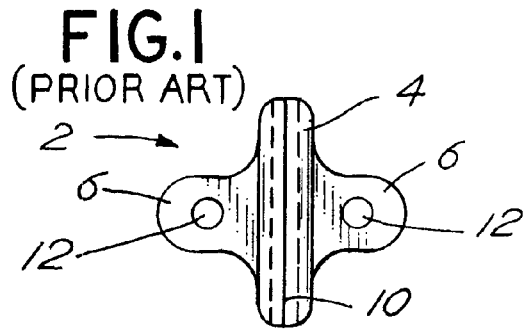
FIG. 1 is a top view of a prior art catheter anchor.
Figure 2:
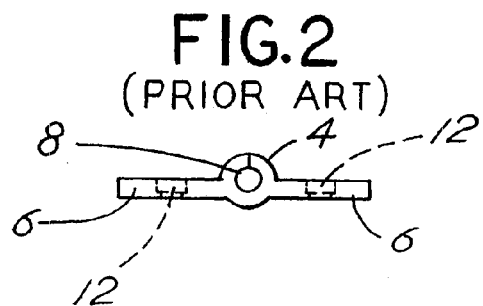
FIG. 2 is an end view of the prior art catheter anchor of FIG. 1.

Referring to FIG. 5, a preferred embodiment of the medical catheter anchor is shown generally labeled 22.

Anchor 22 comprises a shell or sleeve 24 and a pair of wings 26. Anchor 22 is preferably molded of silicone or any other flexible polymeric material such as urethane or other materials as will be clear to those skilled in the art.

Referring to FIGS. 5–8, the preferred sleeve 24 is essentially a cylindrical tube 28 that extends along a longitudinal centerline 30. Tube 28 has a first end 32 and a second end 34 with a channel 36 extending through tube 28 from first end 32 to second end 34. Channel 36 is preferably circular in cross-section and preferably is centered on the longitudinal centerline 30 of the tube 28. Although this is the preferred embodiment, it is to be understood that other cross-sections could also be used as for example oval, "egg" shaped, square, rectangle, pentagon shaped, hexagonal, octagonal, to name but a few possibilities. Further, channel 36 may be located offset from the longitudinal centerline 30 of tube 28. Channel 36 is defined by the inside surface 38 of tube 28. In the preferred embodiment, the diameter of channel 36 is just slightly larger than the diameter of the catheter 14 that is intended to be secured by the anchor 22.

In the preferred embodiment, first and second ends 32, 34 are tapered away from the center 40 of anchor 22 in tapered portions 42. Tapering means that the diameter of the outer surface 44 decreases as the distance from center 40 increases. This tapering allows first and second ends 32, 34 to act as a strain relief for the catheter 14 placed therein as will be explained hereafter.

A slot 46 is preferably formed in the outer surface 44 between wings 26. Slot 46 is preferably elongated in the direction of longitudinal centerline 30 and preferably extends from the outer surface 44 entirely through tube 28. Slot 46 has side edges 48, in an unstressed configuration, that form an angle to each other. As described hereafter, bringing wings 26 together causes the side edges 48 to come into full surface contact with each other. It is acceptable for side edges 48 to just barely touch each other. The key is for side edge 48 to not be compressed together so that hoop stresses are avoided. Side edges 48 define the side dimensions of slot 46.

Figure 13:
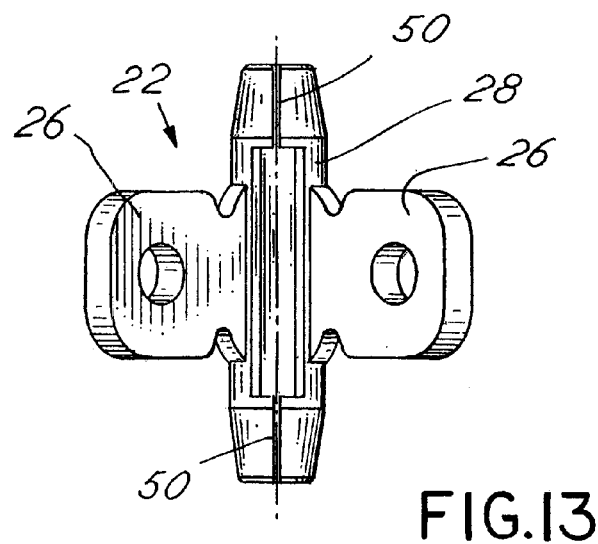
FIG. 13 is a top view of an alternate embodiment of the anchor of FIG. 5.

In an alternate embodiment shown in FIG. 13, a slit 50 extends through tube 28. Slit 50 preferable extends radially from the longitudinal centerline 30. Slit 50 allow the catheter 14 to be place in channel 36 by slightly deforming slit 50 to open and allow the catheter 14 to be passed through slit 50 into channel 36.

A pair of wings 26 extend from the outer surface 44 of tube 28. In the preferred embodiment, the angle between the wings 26 is about 90°. This configuration allows for ease of use by the surgeon as will explained hereafter. Further, this provides a smaller projected footprint for the device which allows the surgeon more room to work with the anchor 22 in the pocket 20.

It is important that the wings 26 be sufficiently separated in the unstressed position so that as the wings 26 are brought together, there is sufficient stress generated to adequately frictionally hold the catheter 14 within the anchor 22. Additionally, the angle between the wings 26 could exceed 90°. In fact, it is within the scope of this invention that the angle between wings 26 could be as large as almost 360° although angles larger than 180° would be difficult to work with by the surgeon.

Figure 3:
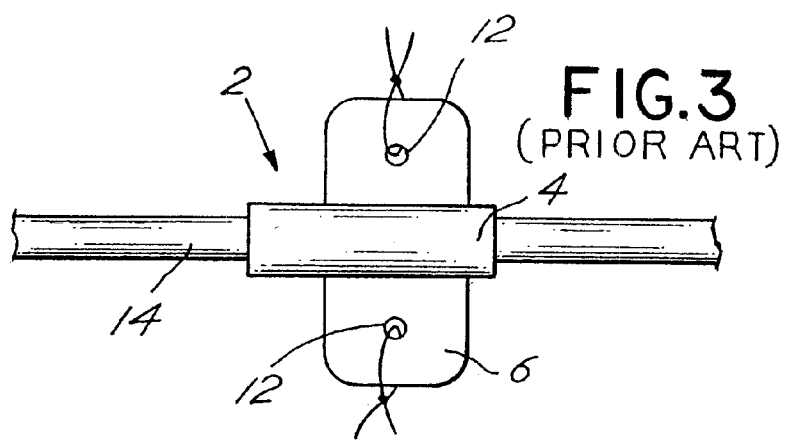
FIG. 3 is a top view of the prior art catheter anchor of FIG. 1 in use.
Figure 4:
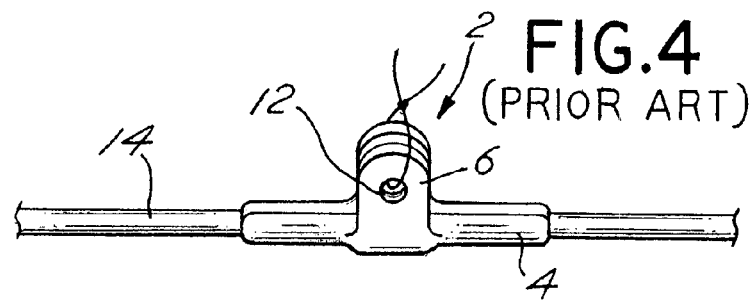
FIG. 4 is a side view of the prior art catheter anchor of FIG. 1 in use.
Figure 9:
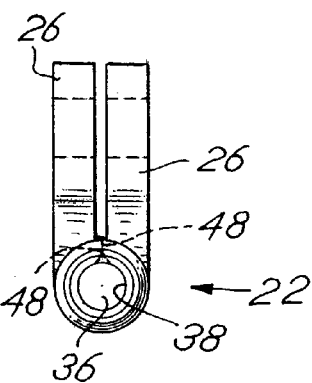
FIG. 9 is an end view of the anchor of FIG. 5 in its closed position.

Wings 26 include opposed sidewalls 52. In the preferred embodiment, wings 26 extend substantially radially from outer surface 44 along radials from the longitudinal centerline 30. Wings 26 are preferably substantially planar with the planes being substantially parallel to the longitudinal centerline 30. As shown in FIG. 3, wings 26 preferably form an acute angle to each other.

In addition, the width "A" of wings 26 preferably exceeds about 30% of the total length "B" of the anchor 22. (FIG. 8) With these ratios, the area of the anchor 22 that causes fixation to the catheter 14 is increased over previously know designs. The wider dimensions of width "A" combined with slot 46 allows a greater area within slot 46 to radially compress into contact with catheter 14 than would be possible with a narrower width "A".

Further, the thicker "C" the wings 26, the higher the stress levels that can be applied to the catheter 14. But, patients and doctors prefer to have as small of an anchor 22 as is possible. So, if wings 26 combined are thicker than the outer diameter of the tube 28, the anchor 22 will be larger than would be desirable. Therefore, it is most preferable that the width "C" be about equal to half the diameter of the tube 28. (FIG. 7) In this way, the maximum stress can be applied to grip the catheter 14 without increasing the overall dimensions of the anchor 22.

Wings 26 each have a suture eyelet 54 and a pair of opposed suture indents 56. Suture eyelets 54 preferably extend entirely through wings 26 for a purpose that will be explained hereafter. Suture indents 56 extend into the sidewall 52 of wings 26 for a purpose that also will be explained hereafter. In the preferred embodiment, suture indents 56 are located as close to outer surface 44 as possible. This increases stress on the catheter 14 when a suture is applied as will be described hereafter. We have found that the normal stress between the catheter 14 and the anchor 22 is inversely proportional to the distance between the centerline of the catheter 14 and the location of the point where the wings 34 are fixed together. The friction between the catheter 14 and the anchor 22 is proportional to the normal stress between the catheter 14 and the anchor 22. Friction is what holds the catheter 14 in a fixed relationship to the anchor 22.

Although wings 26 are preferably substantially planar, they need not be so. Other configurations of wings 26 can be used. Whatever the configuration of wings 26, wings 26 have three key functions. First, wings 26 cooperate with slot 46 to change the effective circumference of tube 28 to cause a radially compressive force on a catheter 14 when wings 26 are brought together. Second, wings 26 provide a means for securing the anchor 22 to tissue 18. The use of wings 26 eliminated the need to suture the tube 28 directly to the tissue 18 with the concomitant possibility of cutting or occluding the catheter 14. Finally, wings 26 are "handles" that allow the surgeon to grasp and manipulate the anchor 22.

Catheters 14 are typically manufactured to specifications including the minimum radius about which the catheter 14 must bend without permanent change in shape, kinking or fracture. Where the catheter 14 exits the anchor 22 at the sleeve 24 at an angle to the longitudinal centerline 30, as shown in FIGS. x and y, the tapered first and second ends 32, 34 are pliable and allow the first and second ends 32, 34 to deform slightly in the direction that the catheter 14 is going. This causes the first or second end 32, 34 to contour to the direction that the catheter 14 is going as it leaves the anchor 22. In this way, the strain on the catheter 14 from deviating from the longitudinal axis is not concentrated at the point where the catheter 14 leaves first or second end 32, 34, but is instead distributed over the entire tapered portion 42.

Figure 10:
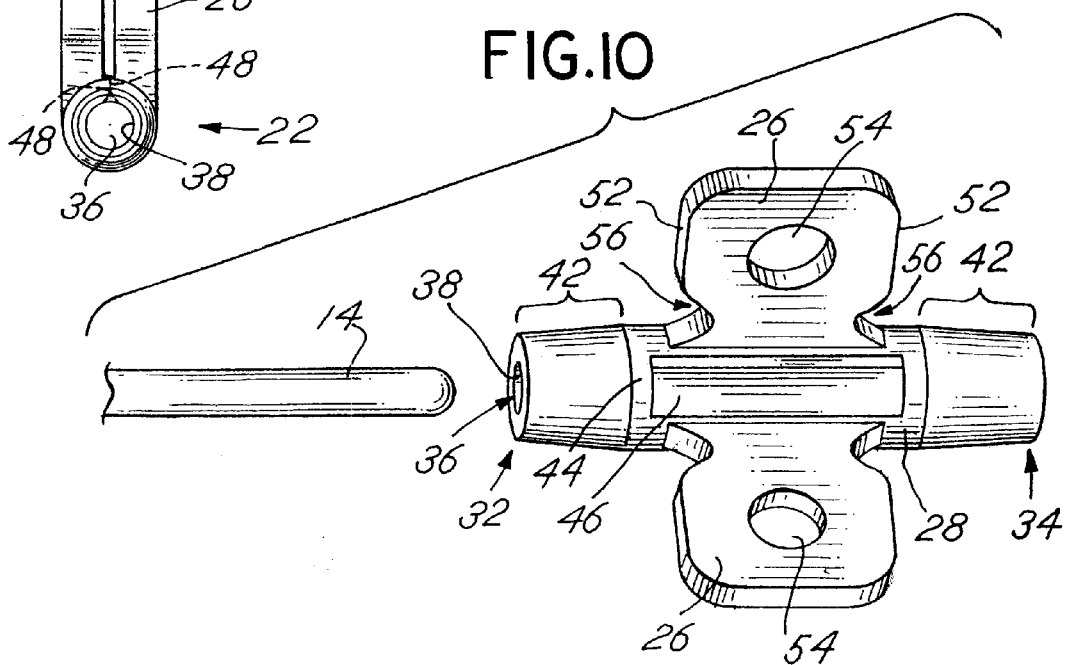
FIG. 10 is a perspective view of the preferred anchor of FIG. 5 ready to receive a catheter.

In use, catheter 14 is threaded through anchor 22. (FIG. 10) Catheter 14 is placed in central channel 36 by threading catheter 14 into either first or second end 32, 34, passing catheter 14 through central channel 36 and out the respective other of first or second end 32, 34. The present invention allows the tolerance between the catheter 14 and the inside surface 38 to be larger than with prior anchors so that the anchor 22 can slide down the catheter to the desired position. In the embodiment having a slit 50, the catheter 14 can be placed in anchor 22 by opening slit 50 and placing catheter 14 into central channel 36 so that the longitudinal axis 54 of catheter 14 is coaxial with the longitudinal centerline 30 of tube 28.

Figure 11:
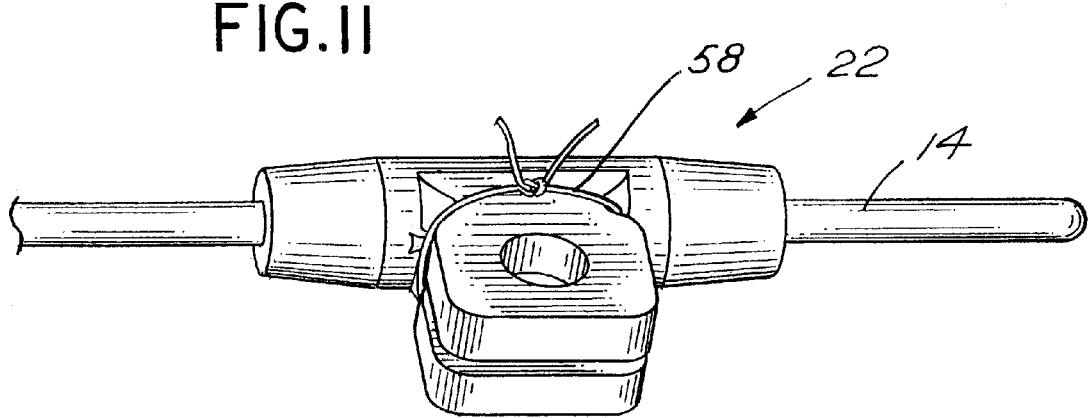
FIG. 11 is a perspective view of the preferred anchor of FIG. 5 with the catheter in place and the wings sutured together.

The wings 26 should be sutured together as shown in FIG. 11 by placing a suture 58 around the indents 56 and pulling the knot so that the wings 26 lie flat against each other. As wings 34 are pulled together, the side edges 48 of slot 46 come together. Preferably, just as the wings 34 come together, side edges 48 will come together. In this way, no hoop stresses will be present as wings 34 come together. As a result, virtually all the stress introduced into the anchor 22 by bringing wings 34 together will be applied to holding catheter 14 in frictional contact within anchor 22.

Further, because side edges 48 meet only when wings 34 come together, there is no chance of "over-tightening" the anchor 22 so that material will be directed inwardly into contact with the catheter 14 to pinch, occlude or otherwise block catheter 14.

In an unstressed configuration, tube 28 has a certain outer circumference. Slot 46 represents a discontinuity in the material in the circumference of tube 28 when tube 28 is in the unstressed configuration. When the side edges 48 are brought together into full surface contact, because the width of slot 46 is eliminated, the circumference of tube 28 will be smaller than when tube 28 is in an unstressed configuration. Because of the direct relationship between circumference and radius, as the circumference decreases, the radius decreases. If the radius of tube 28 when wings 26 are brought together is less than the outer radius of catheter 14, then the inner surface 38 of tube 26 will apply compressive normal forces to the outer surface of catheter 14. As a result, catheter 14 will be fixed with respect to the anchor 22.

Slot 46 consists of material omitted from the tube 28. As a result, as side edges 48 come together, no material will be deformed downward into undesired contact with catheter 14. At this time, the inside surface 38 of tube 28 will be moved into gripping contact with the outer surface of catheter 14 to prevent catheter 14 from moving longitudinally with respect to anchor 22.

If slot 46 were not present, as wings 26 are brought together, the space between wings 26 will be reduced. As a result, material in tube 28 between wings 26 would be "folded". Part of this "folded" material would likely be moved into contact with catheter 14 which could pinch or occlude the catheter 14. Although the preferred embodiment of the anchor 22 has a slot 46, it is to be understood that the invention may also be practiced without slot 46.

As mentioned above, the wings 26 are preferable at an acute angle to each other. This makes it easier to suture the wings together as described above because the wings 26 are closer together than they would be if the wings were 180° apart or more.

Figure 12:
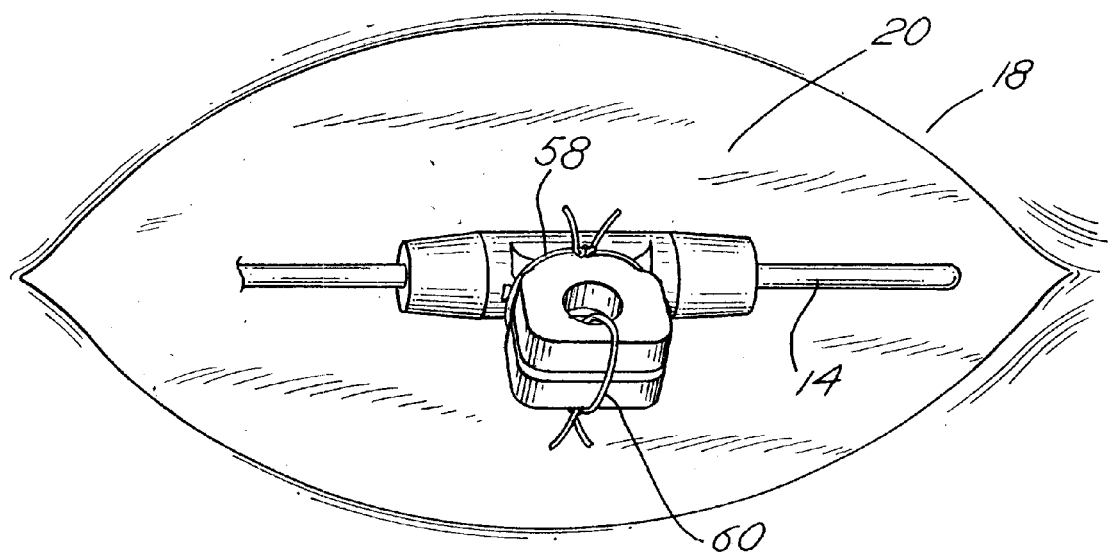
FIG. 12 is a perspective view of the preferred anchor of FIG. 5 in a cavity in a patient with the catheter in place, the wings sutured together and the anchor sutured to the patient's tissue.

Finally, a suture 60 is fastened through the eyelets 54 and tissue 18 at the site of fixation to fasten the anchor 22 to the tissue 18. (FIG. 12) In this way, anchor 22 is prevented from moving relative to the tissue 18 so catheter 14 is also prevented from moving relative to the tissue 18 by the interaction of catheter 14 with the anchor 22 and anchor 22 with the tissue 18.

If the catheter 14 needs to be repositioned, the physician may remove sutures 58 and 60 and slide the catheter 14 to the new desired position. Then sutures 58 and 60 may be reattached as described above.

The invention has been described in connection with specific embodiments. Those skilled in the art will recognize that modifications can be made to the anchor 22 described herein without departure from the true spirit and scope of the invention. In addition, although the anchor 22 has been described in connection with securely positioning a catheter 14, the anchor 22 may also be used to position a lead such as would be used for electrical stimulation of the nervous system or heart.

The true spirit and scope of the inventions of this specification are best defined by the appended claims, to be interpreted in light of the foregoing specification. Therefore, to particularly point out and distinctly claim the subject matter regarded as invention, the following claims conclude this specification.

We claim:

1. A method of securing a catheter to tissue at a fixation site comprising the steps of:
   providing an anchor comprising:
      a tube having an outer surface, a first end and a second end and a channel extending through the tube from the first end to the second end, the tube having a slot that extends from the outer surface entirely through the tube to the channel, the slot having side edges opposed to each other;
      a pair of wings extending from the tube on opposite sides of the slot, the pair of wings separated from each other by an angle, the wings and the slot cooperating so that the opposed side edges of the slot just come together as the wings are brought into contact with each other, each of the pair of wings including opposed sidewalls, each pair of opposed sidewalls having a pair of opposed suture indents in the sidewalls, each of the wings having a suture eyelet;
   placing the catheter in the channel;
   placing a suture around the suture indents and pulling a knot in the suture so that the wings lie flat against each other;
   placing a suture through the suture eyelets and tissue at the site of fixation to fasten the anchor to the tissue.

2. A method as in claim 1 in which the step of placing a suture around the suture indents and pulling a knot in the suture so that the wings lie flat against each other is preceded by and the method further includes the step of manually moving the wings from the position of separation of the wings by the angle to the position of the wings being in contact with each other.

3. A method as in claim 1 or claim 2 in which the step of placing a suture around the suture indents and pulling a knot in the suture so that the wings lie flat against each other further includes pulling the knot so that the side edges are substantially free of compression together.

4. A method as in claim 1 or claim 2 in which the step of placing a suture around the suture indents and pulling a knot in the suture so that the wings lie flat against each other further includes pulling the knot so that the tube is substantially free of hoop stresses.

5. A method as in claim 3 in which the step of placing a suture around the suture indents and pulling a knot in the suture so that the wings lie flat against each other further includes pulling the knot so that the tube is substantially free of hoop stresses.

6. A method as in claim 1 or claim 2 in which the step of providing an anchor includes providing the anchor further with the tube having an inner surface, and the method being a method of acting on a catheter having an outer surface, the steps of the method further including bringing the wings together with the inner surface of the tube applying compressive normal forces to the outer surface of the catheter.

7. A method as in claim 3 in which the step of providing an anchor includes providing the anchor further with the tube having an inner surface, and the method being a method acting on a catheter having an outer surface, the steps of the method further including bringing the wings together with the inner surface of the tube applying compressive normal forces to the outer surface of the catheter.

8. A method as in claim 5 in which the step of providing an anchor includes providing the anchor further with the tube having an inner surface, and the method being a method of acting on a catheter having an outer surface, the steps of the method further including bringing the wings together with the inner surface of the tube applying compressive normal forces to the outer surface of the catheter.

9. A method as in claims 1 or 2 in which the steps of the method result in the catheter being held in a fixed relationship to the anchor.

10. A method as in claim 3 in which the steps of the method result in the catheter being held in a fixed relationship to the anchor.

11. A method as in claim 5 in which the steps of the method result in the catheter being held in a fixed relationship to the anchor.

12. A method as in claim 8 in which the steps of the method result in the catheter being held in a fixed relationship to the anchor.

13. A method as in claims 1 or 2 in which the step of the method of providing an anchor includes providing an anchor with a slit through the tube intersecting the slot and the step of placing the catheter in the channel includes opening the slit.

\* \* \* \* \*